(12) United States Patent
Erdelen et al.

(10) Patent No.: US 6,436,976 B1
(45) Date of Patent: Aug. 20, 2002

(54) AGENTS FOR COMBATING PLANT PESTS

(75) Inventors: Christoph Erdelen, Leichlingen; Wolfram Andersch, Bergisch Gladbach; Klaus Stenzel, Düsseldorf; Astrid Mauler-Machnik, Leichlingen; Wolfgang Krämer, Burscheid, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/701,958

(22) PCT Filed: May 29, 1999

(86) PCT No.: PCT/EP99/03739

§ 371 (c)(1), (2), (4) Date: Dec. 5, 2000

(87) PCT Pub. No.: WO99/63826

PCT Pub. Date: Dec. 16, 1999

(30) Foreign Application Priority Data

Jun. 10, 1998 (DE) .......................................... 198 25 891
Jun. 30, 1998 (DE) .......................................... 198 29 113

(51) Int. Cl.$^7$ ......................... A01N 43/78; A01N 43/64
(52) U.S. Cl. ..................................... 514/365; 514/383
(58) Field of Search ................................ 514/383, 365

(56) References Cited

U.S. PATENT DOCUMENTS

| 3,912,752 | A | 10/1975 | Meiser et al. | ............ | 260/308 R |
| 3,952,002 | A | 4/1976 | Kramer et al. | ........... | 260/308 R |
| 4,147,791 | A | 4/1979 | Meiser et al. | ................. | 424/269 |
| 4,532,341 | A | 7/1985 | Holmwood et al. | ......... | 549/559 |
| 4,626,595 | A | 12/1986 | Holmwood et al. | ......... | 549/559 |
| 4,723,984 | A | 2/1988 | Holmwood et al. | ............ | 71/76 |
| 4,731,385 | A | 3/1988 | Tsuboi et al. | ................ | 514/789 |
| 4,871,390 | A | 10/1989 | Holmwood et al. | ............ | 71/92 |
| 4,904,298 | A | 2/1990 | Holmwood et al. | ............ | 71/92 |

FOREIGN PATENT DOCUMENTS

| CA | 2084140 | 6/1993 |
| EP | 511541 | 9/1996 |
| JP | 63068505 | 3/1988 |
| JP | 63068507 | 3/1988 |
| JP | 63072608 | 4/1988 |
| JP | 63072609 | 4/1988 |
| JP | 63072610 | 4/1988 |
| JP | 3047106 | 2/1991 |
| JP | 3271207 | 12/1991 |
| JP | 4368303 | 12/1992 |
| JP | 8245323 | 9/1996 |
| WO | 92/21241 | 11/1992 |
| WO | 96/03045 | 2/1996 |
| WO | 97/22254 | 6/1997 |
| WO | 97/24032 | 7/1997 |

OTHER PUBLICATIONS

Database Caplus (Online) Accession No. 1993:228245, Document No. 118:228245, Nippon Soda Co.: "Synergistic Agrochemical Pesticide Compositions Containing Amines and Ergosterol Biosynthesis Inhibitors" XP002900600, Zusammenfassung & JP 05 017311 A, Jan. 26, 1993, RN 147576–25–8; RN 147576–27–0.

Database Caplus (Online) Accession No. 1992:607190, Document NO. 117:207190, Takeda Yakuhin Kogyo K.K.: "Insecticidal and Fungicidal Compositions Containing Guanidines" XP002900601, Zusammenfassung & JP 04 108704 A, Apr. 9, 1992.

Database Caplus (Online) Accession No. 1993:488888, Document No. 119:88888, Takeda Chemical Industries, Ltd.: "Agrochemical Compositions Containing Condensed Heterocycle–Containing Amides and Other Active Ingredients" XP002900602, Zusammenfassung & JP 05 039205 A, Feb. 19, 1930.

Database Caplus (Online) Accession No. 1992:545353, Document No. 117:145353, Takeda Chemical Industries, Ltd.: "Synergistic Insecticide Compositions Containing Guanidines and Organophosphates" XP002900603, Zusammenfassung & JP 04 112805 A, Apr. 14, 1992.

Database Caplus (Online), Accession No. 1992:545352, Document No. 117:145352, Takeda Chemical Industries, Ltd.: "Synergistic Insecticide Compositions Containing Guanidines and Carbamates" XP002900604, Zusammenfassung & JP 04 112804 A, Apr. 14, 1992.

Planzenschuts und Schadlengsbekämpfung, (month unavailable) 1977, pp. 140–153, Georg Thieme–Verlag, Sluttgart.

*Primary Examiner*—Allen J. Robinson
(74) *Attorney, Agent, or Firm*—Joseph C. Gil; John E. Mrozinski, Jr.

(57) ABSTRACT

The present invention relates to compositions for controlling plant pests, which contain the compound of the formula (I)

(I)

$$\text{Cl}-\underset{S}{\overset{N}{\triangleleft}}-CH_2-\underset{H}{\overset{}{N}}-\underset{\underset{NO_2}{\overset{\|}{N}}}{C}-\underset{H}{\overset{}{N}}-CH_3$$

in a mixture with fungicidally active compounds, except for cyclopropylcarboxamide derivatives and azolylmethylcycloalkanes.

4 Claims, No Drawings

AGENTS FOR COMBATING PLANT PESTS

This application is a 371 of PCT/EP99/03939, filed May 29, 1999.

The present invention relates to pesticides which comprise an active compound combination of the compound of the formula (I)

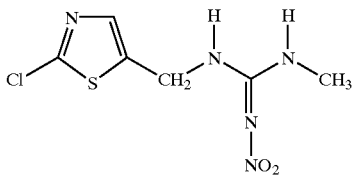
(I)

with fungicides.

Fungicidally active compounds, such as azole derivatives, aryl benzyl ethers, benzamide, morpholine compounds and other heterocycles, are known (cf. K. H. Büchel "Pflanzenschutz und Schädlingsbekämpfung", pages 140 to 153, Georg Thieme-Verlag, Stuttgart 1977, EP published specification 0 040 345, German Offenlegungsschrift 2 324 010, German Offenlegungsschrift 2 201 063, EP published specification 0 112 284, EP published specification 0 304 758 and DD patent specification 140 412).

Mixtures of certain nitromethylene derivatives with fungicidally active compounds and their use as pesticides in crop protection are already known (U.S. Pat. No. 4,731,385; JP published specifications 63-68507, 63/68505; 63/72 608; 63/72 609, 63/72 610, WO 96/03 045, Japanese patent specification 08 245 323, Japanese patent specification 04 368 303, Japanese patent specification 05 017 311, WO 92/21241, WO 97/22 254). Mixtures of certain open-chain nitromethylenes and nitroguanidines with fungicides are already known (Japanese published specification 30 47 106; U.S. Pat. No. 5,181,587).

Mixtures of cyclopropylcarboxamides with certain nitromethylene or nitroguanidine derivatives are already known (Japanese published specification 3 271 207).

Mixtures of, inter alia, imidacloprid and fungicidally active compounds for use in the protection of materials and against termites, but not for use against plant-damaging pests, are already known (EP published specification 0 511 541). Mixtures of imidacloprid and azolylmethylcycloalkanes, in particular triticonazole, are known from EP published specification 545 834.

However, hitherto it has not been known that nitroguanidine derivatives and fungicides with the exception of cyclopropylcarboxamides and triticonazole have such a mutually beneficial effect in their activity that they are outstandingly suitable as compositions for controlling plant pests, whilst being tolerated well by plants.

The present invention relates to compositions against plant pests which contain the compound of the formula (I)

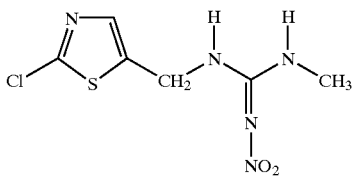
(I)

in a mixture with fungicidally active compounds, except for cyclopropylcarboxamide derivatives and azolylmethylcycloalkanes.

Examples of fungicides in the compositions according to the invention for controlling plant pests which may be mentioned are:

(1) azole derivatives of the formula

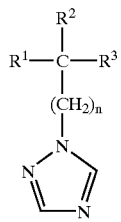
(II)

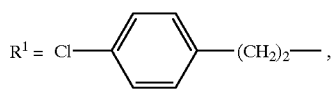
(II-1)

$R^2 = $ ——$C(CH_3)_3$, $R^3 = OH$, $N = 1$,
(TEBUCONAZOLE)

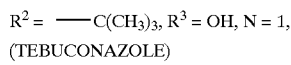
(II-2)

$R^2, R^3 = $ ——$OCH_2CH(n\text{-}C_3H_7)O$——, $n = 1$,
(PROPICONAZOLE)

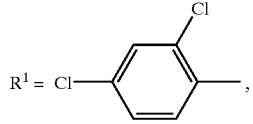
(II-3)

$R^2, R^3, = $ ——$OCH_2CH(CH_3)O$——,
(DIFENCONAZOLE

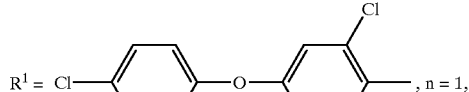
(II-4)

$R^3 = $ ——$OH$, $n = 1$,
(CYPROCONAZOLE)

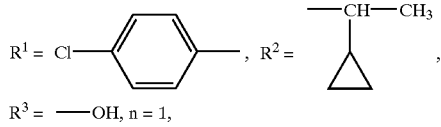
(II-5)

$R^3 = OH$, $n = 1$,
(FLUTRIAFOL)

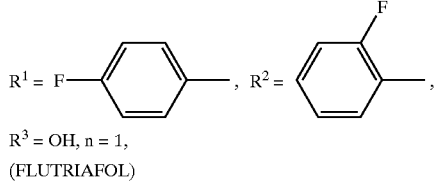
(II-6)

$R^4 = $ ——$(CH_2)_3CH_3$, $R^5 = OH$, $n = 1$,
(HEXACONAZOLE)

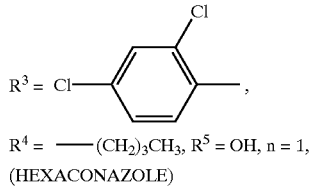
(II-7)

$R^2 = $ ——$(CH_2)_3CH_3$, $R^3 = CN$, $n = 1$,
(MYCLOBUTANIL)

-continued (II-8)
$R^1$ = 2,4-dichlorophenyl,
$R^2$ = —(CH$_2$)$_2$CH$_3$, $R^3$ = H, n = 1,
(PENCONAZOLE)

(II-9)
$R^1$ = 2,4-dichlorophenyl,
$R^2, R^3$ = —OCHCH$_2$CH$_2$—, n = 1,
           |
           OCH$_2$CF$_3$
(FURCONAZOLE)

(II-10)
$R^1$ = 2,4-dichlorophenyl,
$R^2, R^3$ = —OCHCH$_2$O—, n = 1,
           |
           C$_2$H$_5$
(ETACONAZOLE)

(II-11)
$R^1$ = 2,4-dichlorophenyl,
$R^2, R^3$ = —OCH$_2$CHCH$_2$—, n = 1,
                     |
                     Br
(BROMUCONAZOLE)

(II-12)
$R^1$ = 2-chlorobenzyl, $R^2$ = 1-chlorocyclopropyl, $R^3$ = OH, n = 1, (II-13)
$R^1$ = 4-fluorophenyl, $R^2, R^3$ = —OCH— (2-chlorophenyl), n = 1, (II-14)
$R^1$ = phenyl,
$R_2$ = —CH$_2$—CH$_2$—(4-chlorophenyl), n = 1, $R^3$ = CN,
(FENBUCONAZOLE)

(II-15)
$R^1$ = 2,4-dichlorophenyl, $R^2$ = CH$_2$OCF$_2$CHF$_2$, $R^3$ = H, n = 1,
(TETRACONAZOLE)

(II-16)
$R^1$ = (4-chlorophenyl)-O-,
$R^2$ = —CH(OH)—C(CH$_3$)$_3$, n = 0, $R^3$ = H,
(TRIADIMENOL)

(II-17)
$R^1$ = (4-chlorophenyl)-O-,
$R^2$ = —CO—C(CH$_3$)$_3$, n = 0, $R^3$ = H,
(TRIADIMEFON)

(II-18)
$R^1$ = 4-phenylphenoxy,
$R^2$ = —CH(OH)—C(CH$_3$)$_3$, n = 0, $R^3$ = H,
(BITERTANOL)

(II-19)
$R^1$ = 2,4-dichlorobenzyl,
$R^2$ = —CH(OH)—C(CH$_3$)$_3$, n = 0, $R^3$ = H,
(DICLOBUTRAZOLE)

(II-20)
$R^1$ and $R^2$ = (2,4-dichlorophenyl)CH=,
             OH
             |
$R^3$ = —CH-tButyl, n = 0,
(DINICONAZOLE)

(2) azole derivatives of the formula (III)
FLUSILAZOLE: bis(4-fluorophenyl)(methyl)(1H-1,2,4-triazol-1-ylmethyl)silane (3) the azole derivative of the formula

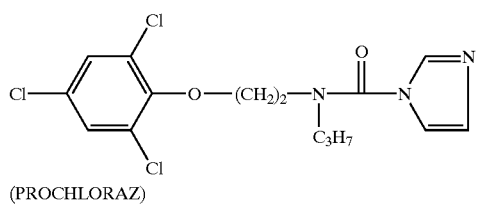

(PROCHLORAZ)

(4) of the compound $S_x$ (V)

(5) the azole derivative of the formula

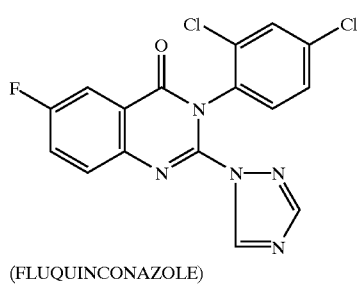

(FLUQUINCONAZOLE)

(6) heterocycles of the formula

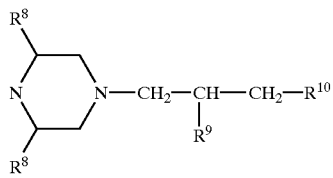

(VII)

X=O, $R^8$=CH$_3$, $R^9$=H, $R^{10}$=C$_{10}$H$_{21}$ (VII-1)

(TRIDEMORPH)

X=O, $R^8$=CH$_3$, $R^9$=H, $R^{10}$=C$_9$H$_{19}$ (VII-2)

(ALDIMORPH)

(VII-3)

X = O, $R^8$ = CH$_3$, $R^9$ = CH$_3$, $R^{10}$ = —⟨phenyl⟩—C(CH$_3$)$_3$ (FENPROPIMORPH)

(VII-4)

X = CH$_2$, $R^8$ = H, $R^9$ = CH$_3$, $R^{10}$ = —⟨phenyl⟩—C(CH$_3$)$_3$ (FENPROPIDIN)

(7) the compound of the formula

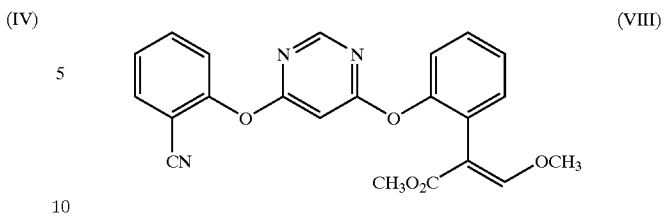

(VIII)

(8) the compound of the formula

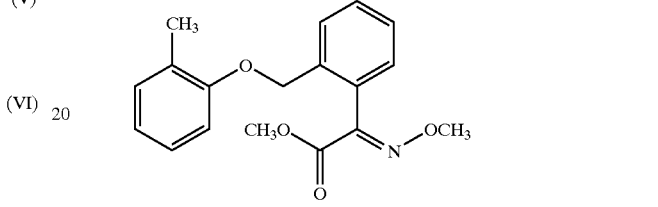

(IX)

(9) the compound of the formula

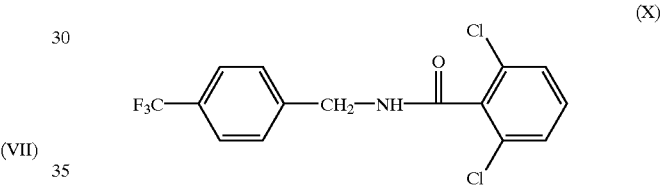

(X)

(10) the compound of the formula

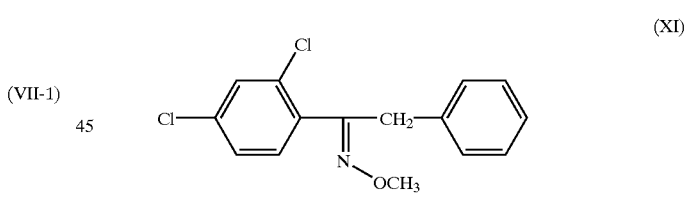

(XI)

(PYRIFENOX)

(11) the compound of the formula (XII)

(FENARIMOL)

(12) the compound of the formula

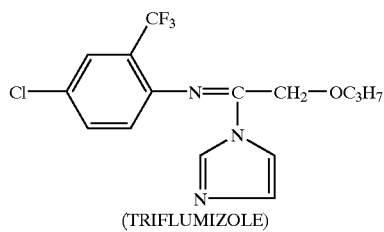

(XIII)

(TRIFLUMIZOLE)

(13) compounds of the formula

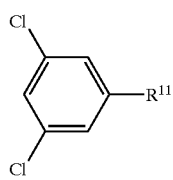

(XIV)

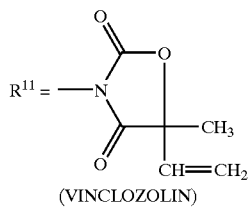

(XIV-1)

(VINCLOZOLIN)

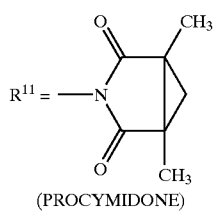

(XIV-2)

(PROCYMIDONE)

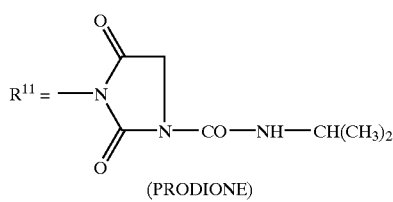

(XIV-3)

(PRODIONE)

(14) compounds of the formula

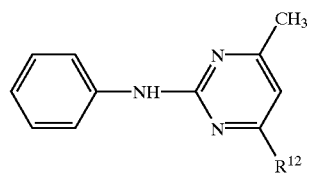

(XV)

$R^{12}=CH_3$     (XV-1)

(PYRIMETHANIL)

$R^{12}=C\equiv C-CH_3$     (XV-2)

(MEPANIPYRIM)

(15) compounds of the formula

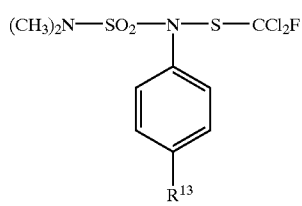

(XVI)

$R^{13}=H$     (XVI-1)

(DICHLOFLUANID)

$R^{13}=CH_3$     (XVI-2)

(TOLYLFLUANID)

(16) the compound of the formula

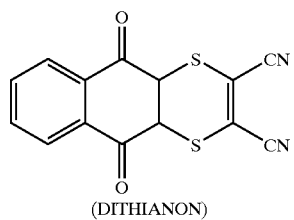

(XVII)

(DITHIANON)

(17) the compound of the formula

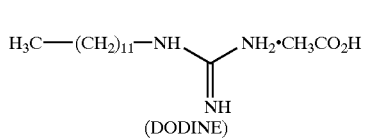

(XVIII)

(DODINE)

(18) the compound of the formula

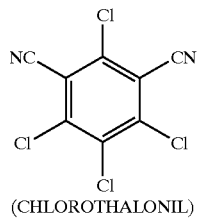

(XIX)

(CHLOROTHALONIL)

(19) the compound of the formula (XX)

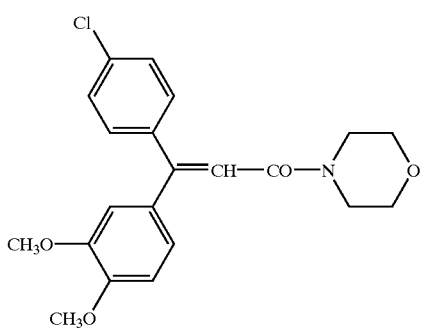

(DIMETHOMORPH)

(20) the compound of the formula

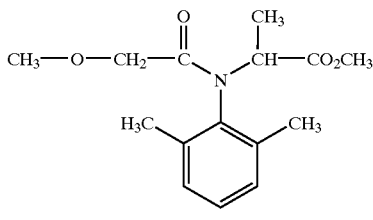

(METALAXYL)

(21) the compound of the formula

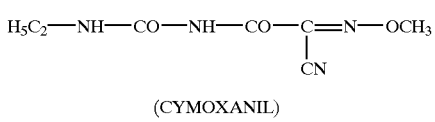

(CYMOXANIL)

(22) the compound of the formula (XXIII)

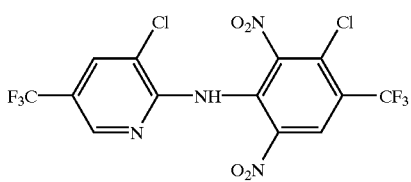

(FLUAZINAM)

(23) the compound of the formula (XXIV)

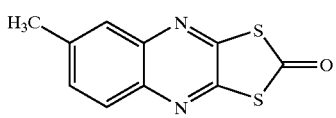

(24) compounds of the formula $$Cl_3C-S-R^{14}$$ (XXV)

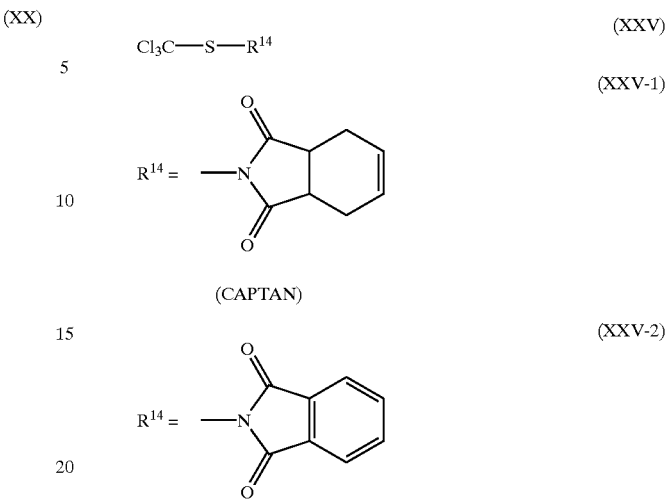

(25) the compound of the formula

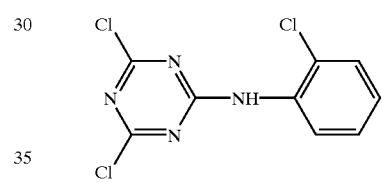

(ANILAZIN)

(26) the compound of the formula (XXVII)

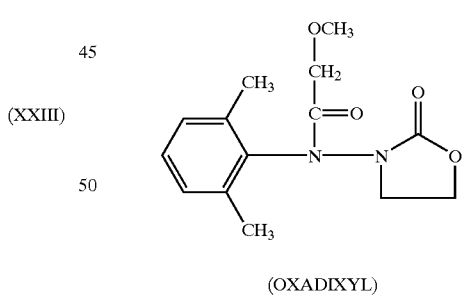

(OXADIXYL)

(27) the compound of the formula (XXVIII)

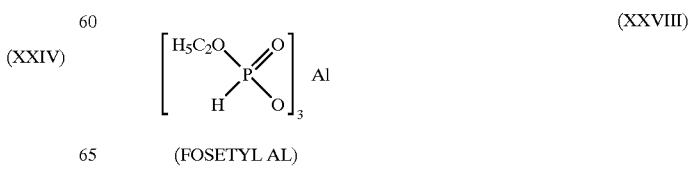

(FOSETYL AL)

(28) the compound of the formula
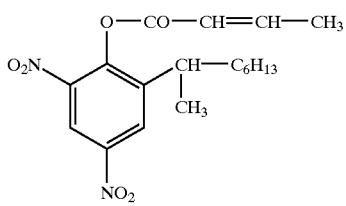
(DINOCAP)
(29) the compound of the formula
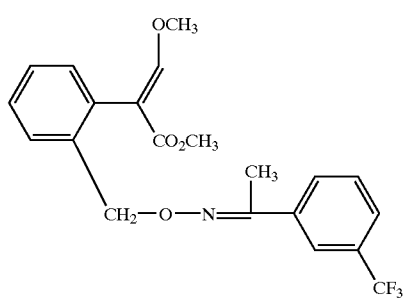
(30) the compound of the formula
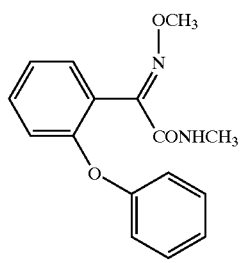
(31) the compound of the formula
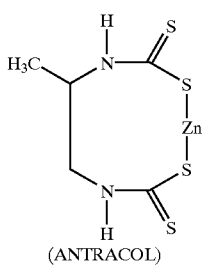
(ANTRACOL)
(32) compounds of the formula
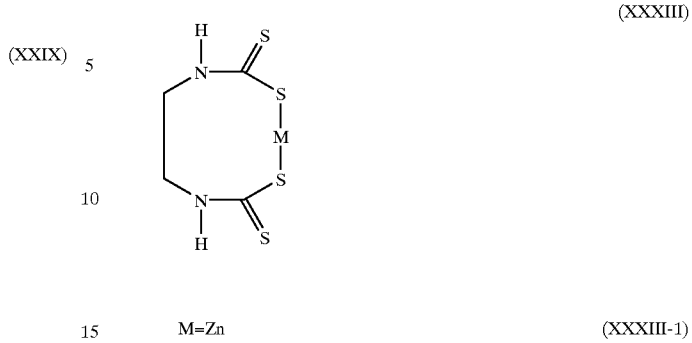
M=Zn            (XXXIII-1)
(ZINEB)
M=Mn           (XXXIII-2)
(MANEB)
M=Mn/Zn        (XXXIII-3)
(MANCOZEB)
(33) the compound of the formula
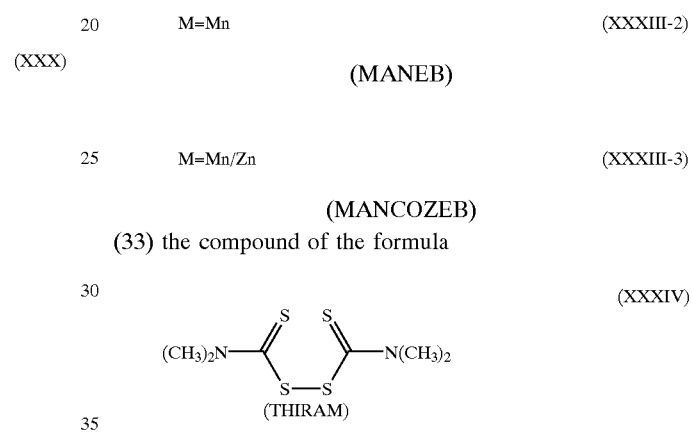
(THIRAM)
(34) the compound of the formula
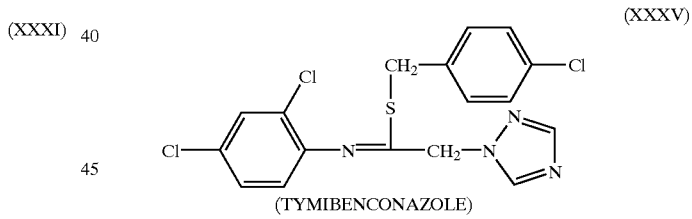
(TYMIBENCONAZOLE)
(35) the compound of the formula
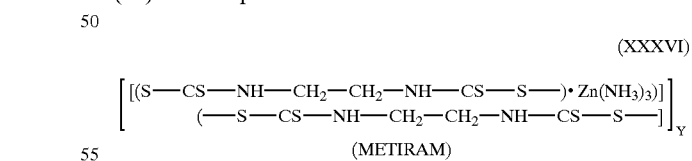
(METIRAM)
(36) the compound of the formula
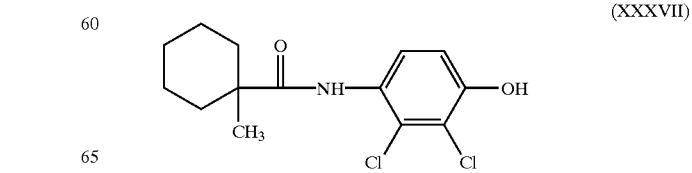

(37) the compound of the formula

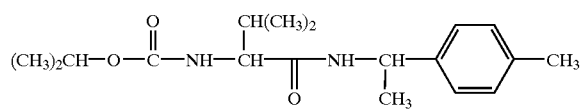

(XXXVIII)

(38) compounds of the formula

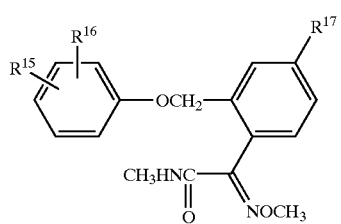

(XXXIX)

in which

R$^{15}$ and R$^{16}$ independently of one another each represent hydrogen, halogen, methyl or phenyl and R$^{17}$ represents hydrogen or methyl,

(39) 8-$^t$butyl-2-(N-ethyl-N-n-propylamino)-methyl-1,4-dioxaspiro[4.5]decane of the formula

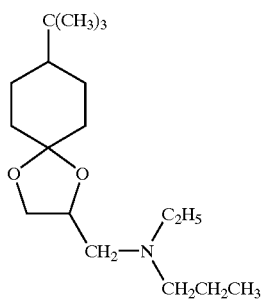

(XL)

(40) the compound of the formula

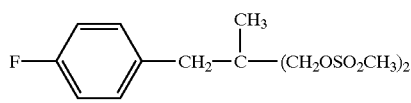

(41) the compound of the formula

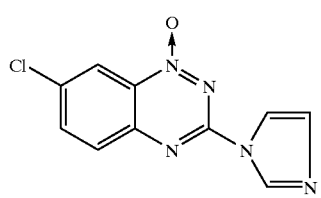

(42) the compound of the formula

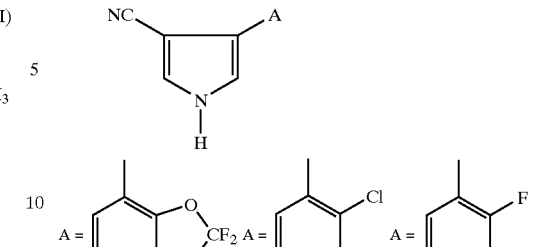

fludioxonil    fenpiclonil

(43) the compound of the formula

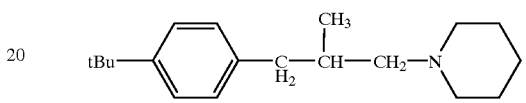

(44) benzimidazoles of the formula

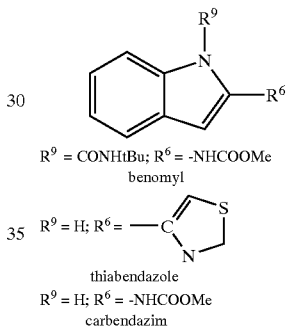

R$^9$ = CONHtBu; R$^6$ = -NHCOOMe
benomyl

R$^9$ = H; R$^6$ = thiabendazole

R$^9$ = H; R$^6$ = -NHCOOMe
carbendazim

(45) the compound of the formula

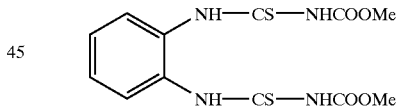

(46) the compound of the formula

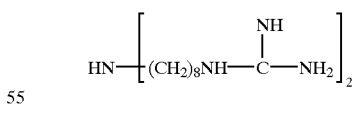

(47) the compound of the formula

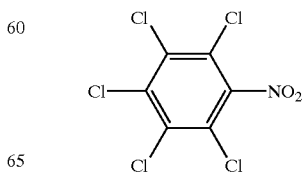

(48) the compound of the formula

(49) the compound of the formula

(50) the compound of the formula

(51) the compound of the formula

IPBC

(52) the compound of the formula

OIT

(53) the compound of the formula

DCOIT

(54) the compound of the formula butylbenzisothiazolinone

(55) the compound of the formula benzothiophene-2-cyclohexyl-
carboxamide S,S-dioxide The active compound of the formula (I) is known from EP published specification 0 375 907.
The fungicidal active compounds are also known.
Thus, for example, the following publications describe:
(1) compounds of the formula (II)
  DE published specification 2 201 063
  DE published specification 2 324 010
  DE published specification 2 737 489
  DE published specification 3 018 866
  DE published specification 2 551 560
  EP 47 594
  DE 2 735 872
(2) the compound of the formula (III)
  EP 68 813
  U.S. Pat. No. 4,496,551
(3) the compound of the formula (IV)
  DE published specification 2 429 523
  DE published specification 2 856 974
  U.S. Pat. No. 4,108,411
(6) compounds of the formula (VII)
  DL 140 041
(7) the compound of the formula (VIII)
  EP 382 375
(8) the compound of the formula (IX)
  EP 515 901
(9) the compound of the formula (X)
  EP 314 422
(10) the compound of the formula (XI)
  EP 49 854
(11) the compound of the formula (XII)
  DE published specification 1 770 288
  U.S. Pat. No. 3,869,456

(13) compounds of the formula (XIV)
DE 2 207 576
U.S. Pat. No. 3,903,090
U.S. Pat. No. 3,755,350
U.S. Pat. No. 3,823,240
(14) compounds of the formula (XV)
EP 270 111
(19) the compound of the formula (XX)
EP219 756
(34) the compound of the formula (XXXV)
U.S. Pat. No. 4,512,989
(38) compounds of the formula (XXXIX)
EP 398 692
(48) compound from
WO 97/27189
(49) compound from
WO 96/16048, this compound can be present in 2 tautomeric forms (A) and (B)

[A]
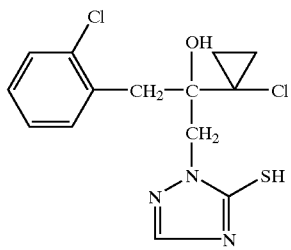

[B]
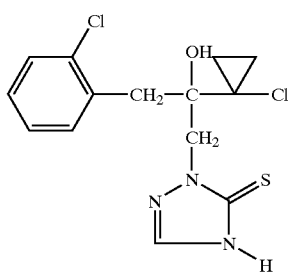

Compounds from the groups (15), (16), (17), (18), (23), (34), (25), (28), (31), (32), (33) and (38) to (47) are described, for example, in K. H. Büchel, "Pflanzenschutz und Schädlingsbekämpfung", pages 121–153, Georg Thieme-Verlag, Stuttgart, 1977. The compound of group (39) is known from EP published specification 281 842. The compound of group (50) is known from WO 97/ 06 171. The compound of group (51) is known from DE-24 33 410. The compounds of groups (52) to (54) are known from W. Paulus, "Microbicides for the Protection of Materials", Chapman & Hall 1993. The compound of group (55) is known from EP-0 512 349.

In addition to the active compound of the formula (I), the active compound combinations according to the invention contain at least one fungicidal active compound, for example selected from the compounds of groups (1) to (55). In addition, they may also contain other active compounds and customary auxiliaries and additives and also diluents.

Preferred fungicidally active compounds in the compositions according to the invention are:
kresoxim-methyl, tebuconazole, metalaxyl, azoxystrobin, triadimenol, bitertanol, fenpicolonil, cyproconazole, propiconazole, fludioxonil and triazoxides.

The mixtures show a clear synergistic effect when the active compounds in the active compound combinations according to the invention are present in certain weight ratios. However, the weight ratios of the active compounds in the active compound combinations can be varied within a relatively wide range. In general,
0.1 to 10 parts by weight, preferably
0.3 to 3 parts by weight of at least one fungicidal active compound, for example from groups (1) to (55),
are present per part by weight of active compound of the formula (I).

The active compound combinations according to the invention have very good fungicidal properties. They can be employed in particular for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling cereal diseases, such as Erysiphe, Cochliobolus, Septoria, Pyrenophora and Leptosphaeria, and against fungal attack on vegetables, grapevines and fruits, for example against Venturia or Podosphaera on apples, Uncinula on grapevines or Sphaerotheca on cucumbers.

The active compound combinations are also highly suitable for controlling animal pests, preferably arthropods, in particular insects, which are encountered in agriculture, in forestry, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Phylloxera*

*vastatrix*, Pemphigus spp., Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

The fact that the active compound combinations are well tolerated by plants at the concentrations required for controlling plant diseases permits the treatment of above-ground parts of plants, of propagation stock and seeds, and of the soil.

The active compound combinations according to the invention can be converted into the customary formulations, such as solutions, emulsions, suspensions, powders, foams, pastes, granules, aerosols, microencapsulations in polymeric compounds and in coating compositions for seeds, and ULV formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane, or paraffins, for example petroleum fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers refer to those liquids which are gaseous at normal temperature and under atmospheric pressure, for example aerosol propellants, such as halogenated hydrocarbons, and also butane, propane, nitrogen and carbon monoxide. Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks, such as calcite, marble, pumice, sepiolite and dolomite, or else synthetic granules of inorganic and organic meals, and granules of organic materials such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers, such as carboxymethylcellulose and natural and synthetic polymers, in the form of powders, granules or latices, such as gum arabic, polyvinyl alcohol and polyvinyl acetate, or else natural phospholipids, such as cephalins and lecithins and synthetic phospholipids, can be used in the formulations. Other possible additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

In the formulations, the active compound combinations according to the invention can be present as a mixture with other known active compounds, such as fungicides, insecticides, acaricides and herbicides, and as mixtures with fertilizers or plant growth regulators.

The active compound combinations can be employed as such, in the form of their formulations or of the use forms prepared therefrom, such as ready-to-use solutions, emulsifiable concentrates, emulsions, suspensions, wettable powders, soluble powders and granules.

The application is carried out in a customary manner, for example by watering, spraying, atomizing, scattering, spreading, dry dressing, wet dressing, liquid dressing, slurry treatment of seeds or incrustation.

In the treatment of parts of plants, the active compound concentrations in the use forms can be varied within a relatively wide range. In general, they are between 1 and 0.0001% by weight, preferably between 0.5 and 0.001%.

In the treatment of seed, the amounts of active compound which are generally required are from 0.001 to 50 g per kilogram of seed, preferably from 0.01 to 10 g. In the treatment of the soil, active compound concentrations of from 0.00001 to 0.1% by weight, preferably from 0.0001 to 0.02% by weight, are required at the site of action.

Furthermore, it has been found that the active compound combinations according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Dermapterans, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as

*Lepisma saccharina.*

Industrial materials are to be understood as meaning, in the present context, non-live materials such as, preferably, plastics, glues, sizes, paper and board, leather, wood and timber products, and coatings.

The materials to be protected against attack by insects are very particularly wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood panelling, windows and doors made of wood, plywood, particle board, joiner's articles, or wood products which, quite generally, are used in the construction of houses or in joinery.

The active compound combinations can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, dyes and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flash point of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of the boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably a-monochloronaphthalene, are used.

The organic oily or oil-type solvents of low volatility having an evaporation number of above 35 and a flash point of above 30° C., preferably above 45° C., can be partially replaced by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters or the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, dyes, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binders. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as butyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylenebenzophenone.

Also particularly suitable as a solvent or diluent is water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides.

Suitable additional components which may be admixed are, preferably, the insecticides mentioned in WO 94/29 268. The compounds mentioned in that document are expressly incorporated into the present application by reference.

Very particularly preferred components which may be admixed are insecticides, such as chlorpyriphos, phoxim, silafluofen, alphamethrin, cyfluthrin, cypermethrin, deltamethrin, permethrin, imidacloprid, NI-25, flufenoxuron, hexaflumuron and triflumuron.

The good pesticidal activity of the active compound combinations according to the invention is demonstrated by the examples below. Whereas the individual active compounds or the known active compound combinations have weaknesses in the pesticidal activity, the tables of the examples below show unambiguously that the activity which was found of the active compound combinations according to the invention is greater than the sum of the activities of the individual active compounds and also greater than the activities of the known active compound combinations.

In the examples below, the active compound of the formula (I)

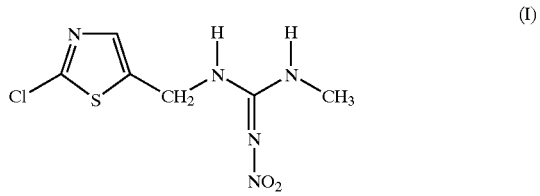

is used.

The fungicidally active compounds which are also used are given in the examples.

EXAMPLE A

Phaedon Larvae Test

Solvent: 7 parts by weight of dimethylformamide

Emulsifier: 1 part by weight of alkylaryl polyglycol ether

To produce a suitable preparation of active compound, 1 part by weight of an active compound or an active compound combination is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following active compound combinations according to the present invention show a synergistically increased activity compared to the individually applied active compounds:

TABLE A (plant-damaging insects)
Phaedon larvae test

| Active compound/active compound mixture | Active compound/active compound mixture concentration in % | Kill in % |
|---|---|---|
| according to formula (I) | 0.00016<br>0.000032 | 20<br>0 |
| kresoxim-methyl | 0.1 | 0 |
| formula (I) + kresoxim-methyl | 0.00016 + 0.1 | 75 |

EXAMPLE B

Plutella Test

Solvent: 7 parts by weight of dimethylformamide

Emulsifier: 1 part by weight of alkylaryl polyglycol ether

To produce a suitable preparation of active compound, 1 part by weight of an active compound or an active compound combination is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with caterpillars of the diamondback moth (*Plutella xylostella*) while the leaves are still moist.

After the desired period of time, the kill in % is determined. 100% means that all caterpillars have been killed; 0% means that none of the caterpillars have been killed.

In this test, for example, the following active compound combinations according to the present invention show a synergistically increased activity compared to the individually applied active compounds:

EXAMPLE C

*Heliothis virescens* Test

Solvent: 7 parts by weight of dimethylformamide

Emulsifier: 1 part by weight of alkylaryl polyglycol ether

To produce a suitable preparation of active compound, 1 part by weight of an active compound or an active compound combination is mixed with the stated amounts of solvent and emulsifier, and the concentrate is diluted with water to the desired concentration.

Soya bean shoots (*Glycine max*) are treated by being dipped into the active compound preparation of the desired concentration and are populated with *Heliothis virescens* caterpillars while the leaves are still moist.

After the desired period of time, the kill in % is determined. 100% means that all caterpillars have been killed; 0% means that none of the caterpillars have been killed.

In this test, for example, the following active compound combinations according to the present invention show a synergistically enhanced activity in comparison to the individually applied active compounds:

TABLE B (plant-damaging insects)
Plutella test

| Active compound/active compound mixture | Active compound/active compound mixture concentration in % | Kill in % |
|---|---|---|
| 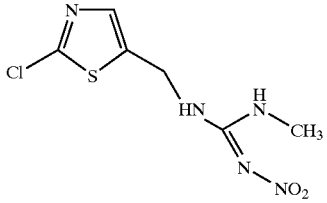<br>according to formula (I) | 0.0008 | 0 |
| 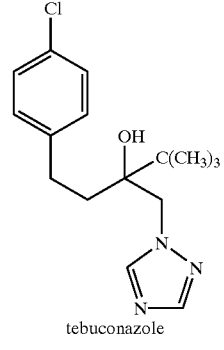<br>tebuconazole | 0.02 | 0 |
| 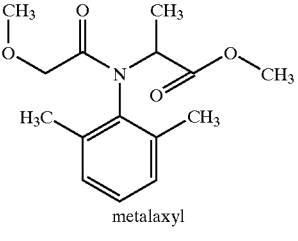<br>metalaxyl | 0.1 | 0 |
| formula (I) + tebuconazole | 0.0008 + 0.02 | 100 |
| formula (II) + metalaxyl | 0.0008 + 0.1 | 100 |

TABLE C

*(plant-damaging insects)*
Heliothis virescens test

| Active compound/active compound mixture | Active compound/active compound mixture concentration in % | Kill in % |
|---|---|---|
| 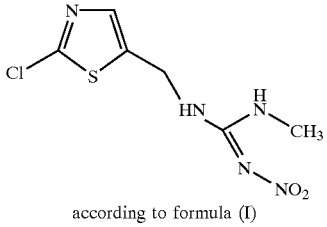 according to formula (I) | 0.00016 | 50 |
| 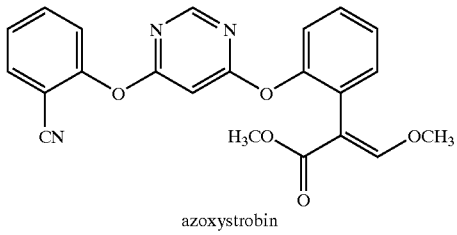 azoxystrobin | 0.0008 | 0 |
| formula (I) + azoxystrobin | 0.00016 + 0.0008 | 100 |

EXAMPLE D

Nephotettix Test

Solvent: 7 parts by weight of dimethylformamide

Emulsifier: 1 part by weight of alkylaryl polyglycol ether

To produce a suitable preparation of active compound, 1 part by weight of an active compound or an active compound combination is mixed with the stated amounts of solvent and emulsifier, and the concentrate is diluted with water to the desired concentration.

Rice seedlings (*Oryza sativa*) are treated by being dipped into the active compound preparation of the desired concentration and are populated with the green rice leaf hopper (*Nephotettix cincticeps*) while the leaves are still moist.

After the desired period of time, the kill in % is determined. 100% means that all the leaf hoppers have been killed; 0% means that none of the leaf hoppers have been killed.

In this test, for example, the following active compound combinations according to the present invention show a synergistically enhanced activity in comparison to the individually applied active compounds:

TABLE D

*(plant-damaging insects)*
Nephotettix test

| Active compound/active compound mixture | Active compound/active compound mixture concentration in % | Kill in % |
|---|---|---|
| 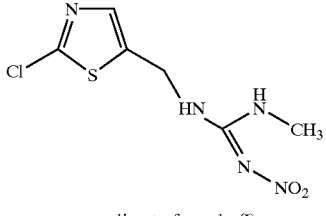 according to formula (I) | 0.00000128 | 0 |

TABLE D-continued (plant-damaging insects)
Nephotettix test

| Active compound/active compound mixture | Active compound/active compound mixture concentration in % | Kill in % |
|---|---|---|
| 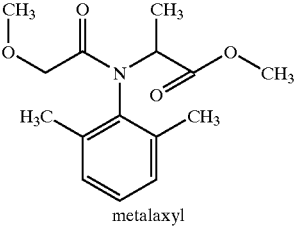<br>metalaxyl | 0.1 | 0 |
| formula (I) + metalaxyl | 0.00000128 + 0.1 | 85 |

EXAMPLE E
Critical Concentration Test/Soil Insects

Test insect: *Spodoptera frugiperda*
Solvent: 4 parts by weight of acetone
Emulsifier: 1 part by weight of alkylaryl polyglycol ether To produce a suitable preparation of active compound, 1 part by weight of the active compound or the active compound mixture is mixed with the stated amounts of solvent and emulsifier, and the concentrate is diluted with water to the desired concentration.

The active compound preparation is mixed intimately with soil. Here, the concentration of the active compound in the preparation is almost irrelevant; only the amount by weight of active compound or active compound mixture per volume unit of soil, which is stated in ppm (mg/l), matters.

Soil is filled into 0.5 pots and these are allowed to stand at 20° C. Immediately after preparation, 3 pre-germinated maize corns are placed into each pot. After the maize corns have emerged, boring sleeves are placed onto the pots. 9 days after preparation, the maize is populated with the test insects. After a further 5 days, the kill in % is determined. 100% means that all test insects have been killed; 0% means that the number of insects which are still alive is the same as for the untreated control.

In this test, for example, the following active compound combinations according to the present invention show a synergistically enhanced activity compared to the individually applied active compounds:

TABLE E

Spodoptera frugiperda test

| Active compound/active compound mixture | Active compound/active compound mixture concentration in % | Kill in % |
|---|---|---|
| 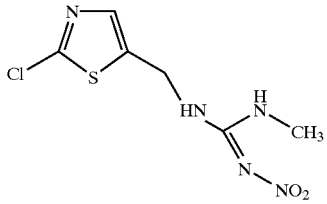<br>according to formula (I) | 1.25<br>0.60<br>0.30 | 100<br>98<br>50 |
| 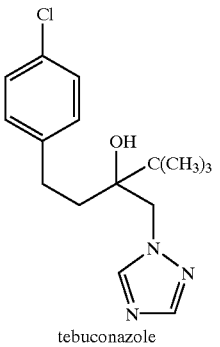<br>tebuconazole | 20.00 | 0 |

TABLE E-continued
Spodoptera frugiperda test
| Active compound/active compound mixture | Active compound/active compound mixture concentration in % | Kill in % |
|---|---|---|
| 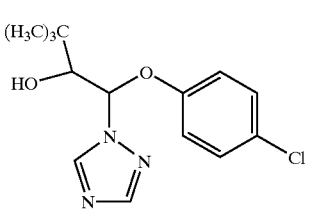<br>triadimenol | 20.00 | 0 |
| 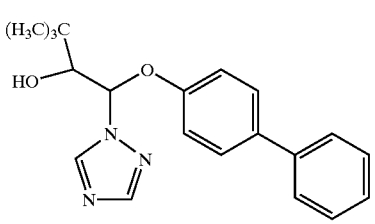<br>bitertanol | 20.00 | 0 |
| 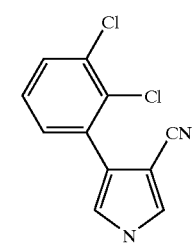<br>fenpiclonil | 20.00 | 0 |
| 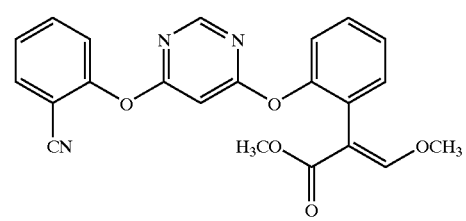<br>azoxystrobin | 20.00 | 0 |
| 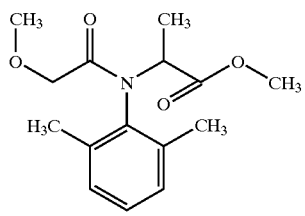<br>metalaxyl | 20.00 | 0 |

TABLE E-continued

Spodoptera frugiperda test

| Active compound/active compound mixture | Active compound/active compound mixture concentration in % | Kill in % |
|---|---|---|
| 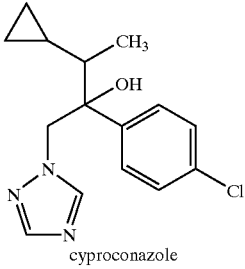<br>cyproconazole | 20.00 | 0 |
| 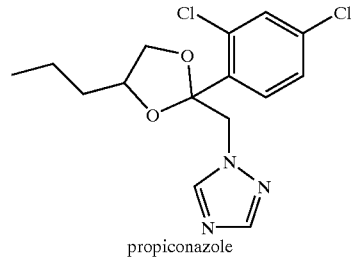<br>propiconazole | 20.00 | 0 |
| formula (I) + tebuconazole | 1.25 + 20.00 | 100 |
|  | 0.60 + 20.00 | 80 |
|  | 0.30 + 20.00 | 80 |
| formula (I) + triadimenol | 1.25 + 20.00 | 100 |
|  | 0.60 + 20.00 | 80 |
|  | 0.30 + 20.00 | 50 |
| formula (I) + bitertanol | 1.25 + 20.00 | 100 |
|  | 0.60 + 20.00 | 80 |
|  | 0.30 + 20.00 | 80 |
| formula (I) + fenpiclonil | 1.25 + 20.00 | 100 |
|  | 0.60 + 20.00 | 90 |
|  | 0.30 + 20.00 | 80 |
| formula (I) + azoxystrobin | 1.25 + 20.00 | 100 |
|  | 0.60 + 20.00 | 80 |
|  | 0.30 + 20.00 | 0 |
| formula (I) + metalaxyl | 1.25 + 20.00 | 100 |
|  | 0.60 + 20.00 | 95 |
|  | 0.30 + 20.00 | 0 |
| formula (I) + cyproconazol | 1.25 + 20.00 | 100 |
|  | 0.60 + 20.00 | 50 |
|  | 0.30 + 20.00 | 0 |
| formula (I) + propiconazole | 1.25 + 20.00 | 100 |
|  | 0.60 + 20.00 | 90 |
|  | 0.30 + 20.00 | 70 |

EXAMPLE F

Critical Concentration Test/Root-systemic Action

Test insect: *Phaedon cochleariae* larvae

Solvent: 4 parts by weight of acetone

Emulsifier: 1 part by weight of alkylaryl polyglycol ether

To produce a suitable preparation of active compound, 1 part by weight of the active compound or the active compound mixture is mixed with the stated amounts of solvent and emulsifier, and the concentrate is diluted with water to the desired concentration.

The active compound preparation is mixed intimately with soil. Here, the concentration of the active compound in the preparation is almost irrelevant; only the amount by weight of active compound or active compound mixture per volume unit of soil, which is stated in ppm (mg/l), matters.

Soil is filled into 250 ml pots and these are planted with cabbage (*Brassica oleracea*). The active compound or the active compound combination can thus be taken up by the plant roots from the soil and transported into the leaves.

After 7 days, the leaves are populated with the above-mentioned test animals. After a further 3 days, the kill in % is determined. 100% means that all test insects have been killed; 0% means that the number of insects which are still alive is the same as in the untreated control.

In this test, for example, the following active compound combinations according to the present invention show a synergistically enhanced activity compared to the individually applied active compounds:

TABLE F
| Active compound/active compound mixture | Active compound/active compound mixture concentration in % | Kill in % |
|---|---|---|
| 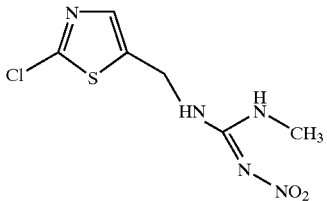<br>according to formula (I) | 1.25<br>0.60<br>0.30 | 100<br>80<br>50 |
| 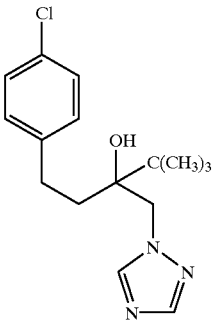<br>tebuconazole | 20.00 | 0 |
| 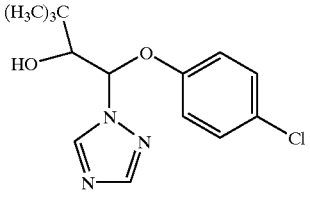<br>triadimenol | 20.00 | 0 |
| 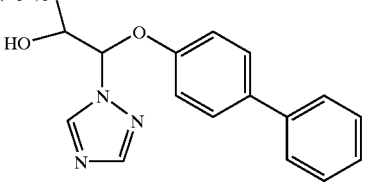<br>bitertanol | 20.00 | 0 |
| 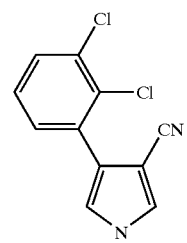<br>fenpiclonil | 20.00 | 0 |

TABLE F-continued

Phaedon cochleariae test

| Active compound/active compound mixture | Active compound/active compound mixture concentration in % | Kill in % |
|---|---|---|
|  azoxystrobin | 20.00 | 0 |
| 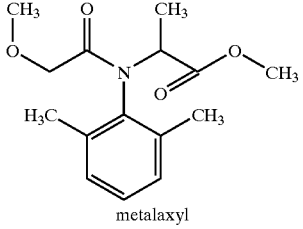 metalaxyl | 20.00 | 0 |
| 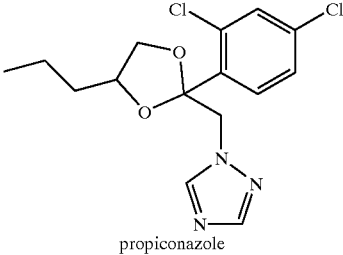 propiconazole | 20.00 | 0 |
| formula (I) + tebuconazole | 1.25 + 20.00 | 100 |
|  | 0.60 + 20.00 | 80 |
|  | 0.30 + 20.00 | 80 |
| formula (I) + triadimenol | 1.25 + 20.00 | 100 |
|  | 0.60 + 20.00 | 100 |
|  | 0.30 + 20.00 | 100 |
| formula (I) + bitertanol | 1.25 + 20.00 | 100 |
|  | 0.60 + 20.00 | 100 |
|  | 0.30 + 20.00 | 70 |
| formula (I) + fenpiclonil | 1.25 + 20.00 | 100 |
|  | 0.60 + 20.00 | 100 |
|  | 0.30 + 20.00 | 70 |
| formula (I) + azoxystrobin | 1.25 + 20.00 | 100 |
|  | 0.60 + 20.00 | 90 |
|  | 0.30 + 20.00 | 50 |
| formula (I) + metalaxyl | 1.25 + 20.00 | 100 |
|  | 0.60 + 20.00 | 100 |
|  | 0.30 + 20.00 | 50 |
| formula (I) + propiconazole | 1.25 + 20.00 | 100 |
|  | 0.60 + 20.00 | 100 |
|  | 0.30 + 20.00 | 90 |

EXAMPLE G

Formula for the Calculation of the Efficacy of a Combination of Two Active Compounds The expected activity for a given combination of two active compounds can be calculated as follows (cf. Colby, S. R., "Calculating Synergistic and Antagonistic Responses of Herbicide Combinations", Weeds 15, pages 20–22, 1967): if X is the efficacy, expressed in % of the untreated control, when applying the active compound A at an application rate of m g/ha, Y is the efficacy, expressed in % of the untreated control, when applying the active compound B at an application rate of n g/ha, E is the efficacy, expressed in % of the untreated control, when applying the active compounds A and B at application rates of m and n g/ha, then $$E = X + Y - \frac{X \times Y}{100}.$$

If the actual fungicidal activity exceeds the calculated value, then the activity of the combination is superadditive, i.e. a synergistic effect exists. In this case, the efficacy which was actually observed must be greater than the value for the expected efficacy (E) calculated from the formula set out above.

Phytophthora Test (Tomato)/Protective

Solvent: 47 parts by weight of acetone

Emulsifier: 3 parts by weight of alkylaryl polyglycol ether

To produce a suitable preparation of active compound, 1 part by weight of the active compound or the active compound mixture is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the commercial active compound preparation at the stated application rate. After the spray coating has dried on, the plants are inoculated with an aqueous spore suspension of *Phytophthora infestans*. The plants are then placed in an incubation cabin at approximately 20° C. and 100% relative atmospheric humidity.

Evaluation is carried out 3 days after the inoculation. 0% means an efficacy which corresponds to that of the control, whereas an efficacy of 100% means that no infection is observed.

The table below shows unambiguously that the activity which was found of the active compound combinations according to the invention is greater than the calculated efficacy (see above), i.e., a synergistic effect is present.

TABLE G/1

| Phytophthora test (tomato)/protective | | |
|---|---|---|
| Active compound/active compound mixture | Active compound/active compound mixture in g/ha | Efficacy in % calculated/found |
| according to formula (I) | 500 | 51 |
| propiconazole | 500 | 5 |
| formula (I) + propiconazole | 500 + 500 | 53/69 |

TABLE G/2

| Phytophthora test (tomato)/protective | | |
|---|---|---|
| Active compound/active compound mixture | Active compound/active compound mixture in g/ha | Efficacy in % calculated/found |
| according to formula (I) | 500 | 55 |

TABLE G/2-continued

Phytophthora test (tomato)/protective

| Active compound/active compound mixture | Active compound/active compound mixture in g/ha | Efficacy in % calculated/found |
|---|---|---|
| 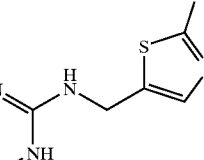 | 500 | 0 |
| triadimenol | | |
| formula (I) + triadimenol | 500 + 500 | 55/63 |

TABLE G/3

Phytophthora test (tomato)/protective

| Active compound/active compound mixture | Active compound/active compound mixture in g/ha | Efficacy in % calculated/found |
|---|---|---|
| 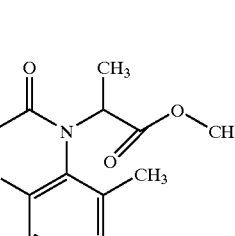 | 50 | 19 |
| according to formula (I) | | |
| | 50 | 42 |
| metalaxyl | | |
| formula (I) + metalaxyl | 50 + 50 | 53/68 |

EXAMPLE H

Sphaerotheca Test (Cucumber)/Protective

Solvent: 47 parts by weight of acetone

Emulsifier: 3 parts by weight of alkylaryl polyglycol ether

To produce a suitable preparation of active compound, 1 part by weight of the active compound or the active compound mixture is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the commercial active compound preparation at the stated application rate. After the spray coating has dried on, the plants are inoculated with an aqueous spore suspension of *Sphaerotheca fuliginea*. The plants are then placed in an incubation cabin at approximately 20° C. and 100% relative atmospheric humidity.

Evaluation is carried out 10 days after the inoculation. 0% means an efficacy which corresponds to that of the control, whereas an efficacy of 100% means that no infection is observed.

The table below shows unambiguously that the activity which was found of the active compound combinations according to the invention is greater than the calculated efficacy (see above), i.e., a synergistic effect is present.

TABLE H/1

Sphaerotheca test (cucumber)/protective

| Active compound/active compound mixture | Active compound/active compound mixture in g/ha | Efficacy in % calculated/found |
|---|---|---|
| 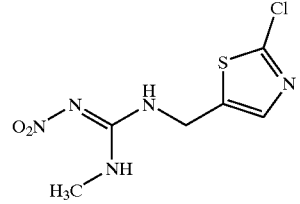<br>according to formula (I) | 10 | 0 |
| 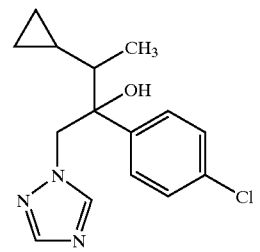<br>cyproconazole | 10 | 70 |
| formula (I) + cyproconazole | 10 + 10 | 70/80 |

TABLE H/2

Sphaerotheca test (cucumber)/protective

| Active compound/active compound mixture | Active compound/active compound mixture in g/ha | Efficacy in % calculated/found |
|---|---|---|
| 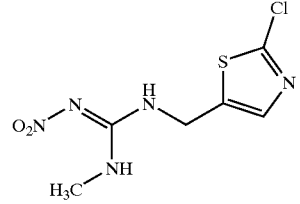<br>according to formula (I) | 500 | 0 |
| 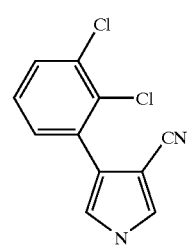<br>fenpiclonil | 500 | 50 |
| formula (I) + fenpiclonil | 500 + 500 | 50/83 |

EXAMPLE I

Botrytis Test (Bean)/Protective

Solvent: 47 parts by weight of acetone

Emulsifier: 3 parts by weight of alkylaryl polyglycol ether

To produce a suitable preparation of active compound, 1 part by weight of the active compound or the active compound mixture is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, 2 small pieces of agar colonized by Botrytis cinerea are placed onto each leaf. The inoculated plants are placed in a dark chamber at approximately 20° C. and 100% relative atmospheric humidity.

2 days after the inoculation, the size of the disease spots on the leaves is evaluated. 0% means an efficacy which corresponds to that of the control, whereas an efficacy of 100% means that no infection is observed.

The table below shows unambiguously that the activity which was found of the active compound combinations according to the invention is greater than the calculated efficacy (see above), i.e., a synergistic effect is present.

TABLE I/1

| | Botrytris test (bean)/protective | |
|---|---|---|
| Active compound/active compound mixture | Active compound/active compound mixture in g/ha | Efficacy in % calculated/found |
| 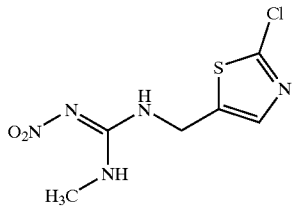<br>according to formula (I) | 10 | 0 |
| 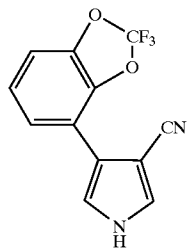<br>fludioxonil | 10 | 40 |
| formula (I) + fludioxonil | 10 + 10 | 40/83 |

TABLE I/2

| | Botrytris test (bean)/protective | |
|---|---|---|
| Active compound/active compound mixture | Active compound/active compound mixture in g/ha | Efficacy in % calculated/found |
| 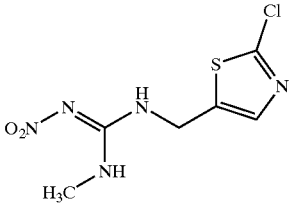<br>according to formula (I) | 100 | 4 |

TABLE I/2-continued

Botrytris test (bean)/protective

| Active compound/active compound mixture | Active compound/active compound mixture in g/ha | Efficacy in % calculated/found |
|---|---|---|
| 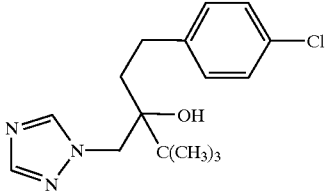<br>tebuconazole | 100 | 80 |
| formula (I) + tebuconazole | 100 + 100 | 81/94 |

EXAMPLE J
*Fusarium culmorum* Test (Wheat)/Seed Treatment

The active compounds are applied as a dry dressing. They are prepared by extending the active compound in question with ground minerals to give a finely pulverulent mixture which ensures even distribution on the surface of the seeds.

For the dressing, the infected seeds are shaken with the dressing in a closed glass bottle for 3 minutes.

2×100 seeds of the wheat are sown at a depth of 1 cm into standard soil, and the wheat is cultivated in a greenhouse at a temperature of approximately 18° C. and at a relative atmospheric humidity of approximately 95% in seed containers receiving 15 hours of light per day.

The evaluation of the plants for symptoms is carried out approximately 3 weeks after sowding. 0% means an efficacy which corresponds to that of the control, whereas an efficacy of 100% means that no infection is observed.

TABLE J

*Fusarium culmorum* test (wheat)/seed treatment

| Active compound/active compound mixture | Active compound/active compound mixture in g/ha | Efficacy in % |
|---|---|---|
| 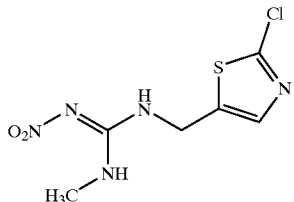<br>according to formula (I) | 75 | 0 |
| 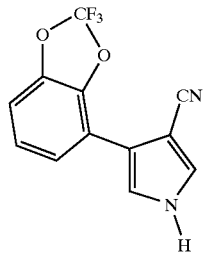<br>fludioxonil | 75 | 0 |

TABLE J-continued

*Fusarium culmorum* test (wheat)/seed treatment

| Active compound/active compound mixture | Active compound/active compound mixture in g/ha | Efficacy in % |
|---|---|---|
| 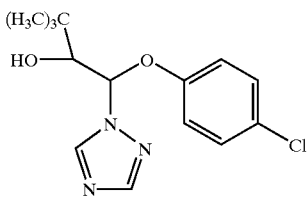 triadimenol | 75 | 13.5 |
| formula (I) + fludioxonil | 37.5 + 37.5 | 38.5 |
| formula (I) + triadimenol | 37.5 + 37.5 | 30.5 |

EXAMPLE K

Puccinia Test (Wheat)/Protective

Solvent: 25 parts by weight of N,N-dimethylacetamide

Emulsifier: 0.6 parts by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of approximately 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

TABLE K

Puccinia (wheat)/protective

| Active compound/active compound mixture | Active compound/active compound mixture in g/ha | Efficacy in % |
|---|---|---|
| 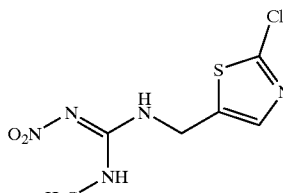 according to formula (I) | 18.75 | 0 |
| 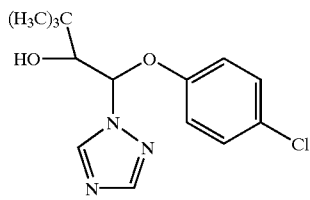 triadimenol | 18.75 | 13 |
| formula (I) + triadimenol | 9.375 + 9.375 | 63 |

EXAMPLE L

*Pyrenophora teres* Test (Barley)/Protective

Solvent: 25 parts by weight of N,N-dimethylacetamide

Emulsifier: 0.6 parts by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are sprayed with a conidia suspension of *Pyrenophora teres*. The plants remain in an incubation cabin at 20° C. and 100% relative atmospheric humidity for 48 hours.

The plants are then placed in a greenhouse at a temperature of approximately 20° C. and a relative atmospheric humidity of approximately 80%.

Evaluation is carried out 7 days after the inoculation. 0% means an efficacy which corresponds to that of the control, whereas an efficacy of 100% means that no infection is observed.

EXAMPLE M

Erysiphe Test (Barley)/Protective

Solvent: 25 parts by weight of N,N-dimethylacetamide

Emulsifier: 0.6 parts by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

TABLE L

*Pyrenophora teres* test (barley)/protective

| Active compound/active compound mixture | Active compound/active compound mixture in g/ha | Efficacy in % calculated/found |
|---|---|---|
| 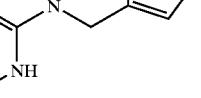<br>according to formula (I) | 62.5<br>18.75 | 0<br>20 |
| 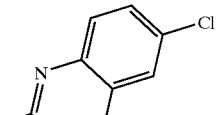<br>triazoxides | 62.5 | 40 |
| 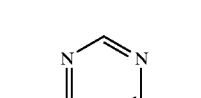<br>azoxystrobin | 18.75 | 0 |
| formula (I) + azoxystrobin | 9.375 + 9.375 | 60 |
| formula (I) + triazoxides | 31.25 + 31.25 | 70 |

TABLE M

Erysiphe test (barley)/protective

| Active compound/active compound mixture | Active compound/active compound mixture in g/ha | Efficacy in % calculated/found |
|---|---|---|
| ![structure: 2-chlorothiazole-nitroguanidine with NHCH3] according to formula (I) | 62.5 | 0 |
| ![structure: kresoxim-methyl] kresoxim-methyl | 62.5 | 0 |
| formula (I) + kresoxim-methyl | 31.25 + 31.25 | 75 |

EXAMPLE N

Critical Concentration Test/Root Systemic Action

Test insect: *Spodoptera frugiperda*

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is mixed intimately with soil. Here, the concentration of the active compound in the preparation is virtually immaterial; only the amount by weight of active compound per volume unit of soil, which is stated in ppm (mg/l), matters. The soil is filled into 250 ml pots and these are allowed to stand at 20° C.

Immediately after preparation, 3 maize corns are placed into each pot. 14 days after the preparation, the test insects are placed into an insect bracket and attached to the plant. 4 days after the infection, the efficacy of the active compound is determined in % by counting the dead and live test insects. The efficacy is 100% if all test insects have been killed; it is 0% if the same number of test insects is alive as in the untreated control.

TABLE N

*Spodoptera frugiperda* test

| Active compound/active compound mixture | Kill in % at active compound/ active compound mixture concentration in ppm |
|---|---|
| ![structure: 2-chlorothiazole-nitroguanidine with NHCH3] according to formula (I) | 0.15 ppm = 50% |
| ![structure: chlorophenyl-cyclopropyl-triazolinethione] compound of group (49) | 5.00 ppm = 0% |
| compound according to formula (I) + compound of group (49) | 0.15 ppm + 5.00 ppm = 80% |

EXAMPLE O

Critical Concentration Test/Soil Insects

Test insect: *Diabrotica balteata*—larvae in the soil

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration. Here, the concentration of the active compound in the preparation is almost irrelevant; only the amount by weight of active compound per volume unit of soil, which is stated in ppm (mg/l), matters. The soil is filled into 0.5 pots and these are allowed to stand at 20° C.

Immediately after preparation, 5 maize corns are placed into each pot. After 3 days, the test insects are placed into the treated soil. After a further 7 days, the efficacy is determined. The efficacy is calculated from the number of maize plants which have emerged.

Active compounds, application rates and results are shown in the table below:

TABLE O

Soil insecticides
*Diabrotica balteata* - larvae in the soil

| Active compound (constitution) | Kill in % at active compound concentrations in ppm |
|---|---|
| 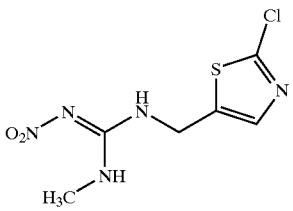 according to formula (I) | 0.15 ppm = 0% |
| 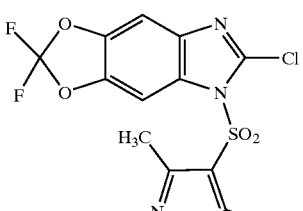 according to (50) | 20.00 ppm = 70% |
| formula (I) + compound according to (50) | 0.15 ppm + 20.00 ppm = 70% |

TABLE P

Soil insecticides
*Diabrotica balteata* - larvae in the soil

| Active compound (constitution) | Kill in % at active compound concentrations in ppm |
|---|---|
| 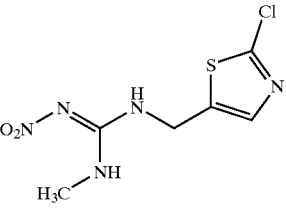 formula (I) | 0.30 ppm = 50% |
| 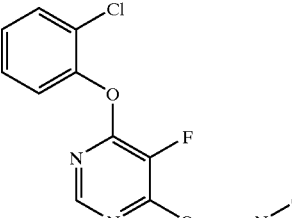 according to (48) | 20.00 ppm = 0% |
| formula (I) + compound according to (48) | 0.15 ppm + 20.00 ppm = 90% |

What is claimed is:

1. A fungicidal and insecticidal composition comprising synergistic effective amounts of a compound of the formula (I)

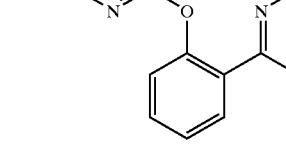

and tebuconazole.

2. The composition of claim 1 comprising from 0.1 to 10 parts by weight of the tebuconazole compound per part by weight of active compound of the formula (I).

3. A process for controlling at least one of fungi and insects, comprising applying an effective amount of the composition of claim 1 to at least one of the fungi, insects or their habitat.

4. A process for preparing a fungicidal or insecticidal composition comprising mixing the composition of claim 1 with at least one of extenders and surfactants.

* * * * *